United States Patent [19]
Johnstone et al.

[11] Patent Number: 5,387,724
[45] Date of Patent: Feb. 7, 1995

[54] SELECTIVE HYDROXYLATION OF PHENOL OR PHENOLIC ETHERS

[75] Inventors: Alexander Johnstone, Little Neston; William R. Sanderson; Robert C. Wasson, both of Penketh, all of United Kingdom

[73] Assignee: Solvay Interox Limited, England

[21] Appl. No.: 133,110

[22] PCT Filed: Apr. 9, 1992

[86] PCT No.: PCT/GB92/00639
§ 371 Date: Oct. 12, 1993
§ 102(e) Date: Oct. 12, 1993

[87] PCT Pub. No.: WO92/18449
PCT Pub. Date: Oct. 29, 1992

[30] Foreign Application Priority Data
Apr. 11, 1991 [GB] United Kingdom ............... 9107655

[51] Int. Cl.⁶ .................... C07C 37/60; B01J 31/00
[52] U.S. Cl. ........................ 568/771; 502/102; 502/104; 568/741; 568/803
[58] Field of Search .............. 568/741, 771, 803; 502/102, 104

[56] References Cited

U.S. PATENT DOCUMENTS

| | | | |
|---|---|---|---|
| 3,416,884 | 12/1968 | Stynes et al. | 502/104 |
| 3,514,490 | 5/1970 | Marlard | 568/771 |
| 5,138,104 | 8/1992 | Takahashi et al. | 568/771 |

FOREIGN PATENT DOCUMENTS

0132783 2/1985 European Pat. Off. .
0170684 7/1993 Japan .

OTHER PUBLICATIONS

*Chemical Abstracts*, vol. 85, No. 24, 13 Dec. 1976, Abstract No. 178465Y.

*Primary Examiner*—Werren B. Lone
*Attorney, Agent, or Firm*—Larson & Taylor

[57] ABSTRACT

Phenols, and related aromatic compounds, phenolic ethers, can be hydroxylated selectively using hydrogen peroxide in the presence of an amorphous or microcrystalline zirconium phosphate catalyst in a solvent containing an aliphatic carboxylic acid. The process is particularly suitable for phenol itself, and advantageously employs a partially dehydrated microcrystalline catalyst obtained by heating an hydrated microcrystalline zirconium phosphate for example at about 100° C. A convenient reaction temperature is 50° to 90° C., and convenient solvent is acetic acid. In an improved method of producing the catalyst, zirconium phosphate is precipitated from an aqueous phosphoric acid solution of zirconium oxychloride in the presence of a cationic phase transfer agent such as an alkylpyridinium salt or tetraalkylquaternary ammonium salt or a nonionic surfactant such as an alcohol ethoxylate.

23 Claims, No Drawings

SELECTIVE HYDROXYLATION OF PHENOL OR PHENOLIC ETHERS

The present invention relates to a process for hydroxylating phenol and more particularly to a process in which phenol is hydroxylated using hydrogen peroxide in the presence of a catalyst.

Phenol is a readily available raw material which can be hydroxylated using aqueous hydrogen peroxide and a catalyst to produce dihydric phenols, and particularly mixtures containing hydroquinone and catechol. However, the introduction of a second hydroxyl substituent onto the aromatic nucleus tends to activate the molecule towards further reaction and this leads to the formation of a mixture of unwanted tarry by-products. Self-evidently it would be desirable to hydroxylate selectively, i.e. favour dihydric phenol formation compared with tarry by-product formation.

A commercial process has been developed for hydroxylating phenol based upon catalysed hydrogen peroxide which tends to produce mixtures containing a major fraction of catechol, but additionally a minor, significant fraction of hydroquinone, typically in a mole ratio of about 3:1. The proportion of tarry by-products has been controlled by limiting very strictly to the use of very low mole ratios of hydrogen peroxide to phenol, but inevitably this restricts the extent of conversion of the phenol and leads to the recycling of an overwhelming fraction of unreacted phenol which in turn reduces the space yield of the plant. It would be desirable to develop a process which enabled a higher proportion of the phenol to be reacted to the desired end-products in each cycle.

It is an object of the present invention to ameliorate or overcome one or more of the difficulties indicated herein with regard to known processes for the catalysed hydroxylation of phenol.

According to the present invention, there is provided a process for the hydroxylation of a substrate comprising a phenol or related aromatic compounds by reaction with hydrogen peroxide in the presence of a catalyst, characterised in that the substrate is a phenol or phenolic ether and the reaction is carried out in a solvent containing an effective amount of an aliphatic carboxylic acid and the catalyst comprises amorphous or microcrystalline zirconium phosphate.

By the use of a process according to the present invention, it is possible to obtain good selectivity of reaction towards the introduction of a single additional hydroxyl substituent around the aromatic nucleus of the substrate, normally ortho or para to the existing substituent.

The substrate can be mono, bi or poly-nuclear and, preferably, is mono-nuclear. The nucleus or nuclei is or are particularly suitably carbocyclic. The most preferred nucleus is benzene. Although the substrate may contain more than one of the relevant substituents namely hydroxyl or ether, it is preferable for only one to be present. A particularly preferred substrate comprises phenol itself. The substrate nucleus may be further substituted, if desired, for example by an alkyl group, $R_a$, preferably short chain such as methyl or ethyl. When the substituent is an ether, suitably of formula —$OR_b$, $R_b$ is suitably alkyl and preferably short chain alkyl such as methyl or ethyl.

The catalyst employed in processes of the present invention comprises an amorphous or microcrystalline zirconium phosphate. The catalyst can be produced by the two stage method described by A. Clearfield and D. S. Thakur in Applied Catalysis, 26,1 (1986). In the first stage, zirconium oxychloride ($ZrOCl_2$) is reacted with excess phosphoric acid in an aqueous medium, conveniently at laboratory ambient temperature or thereabouts, and amorphous zirconium phosphate precipitates from solution. In the second stage, a microcrystalline form is obtained by digesting the filtered amorphous material with concentrated phosphoric acid solution, at above ambient temperature, for example from 80 to reflux temperature, for at least 24 hours and often between 48 and 100 hours. The crystalline material so obtained is hydrated.

Preferably the microcrystalline form is at least partially dehydrated before it is employed. Dehydration can be effected conveniently by heating the material, suitably in an oven. The effectiveness of the resultant catalyst appears to correspond to at least some extent with the temperature employed. A convenient temperature range extends up to about 500° C. Within that range it is preferably to employ a temperature of up to 300° C., because the catalyst so produced tends to be more active than if a higher temperature is employed. It is believed that the change in activity may be attributable to a change in the crystal structure which begins to occur in the region of about 250° C. and which is complete by about 350° C. This change in structure is believed to be attributable to the removal of water of hydration from within the structure of the crystal, whereas at temperatures below about 250° C., the drying removes adsorbed water. It is particularly preferable to select a dehydration temperature in the range of about 50° to about 300° C. It has been found that the catalyst obtained by heating at or around 100° C. is especially effective, in that it produces only a relatively small proportion of by-products. It will, however, be understood that the invention is not dependent upon any particular belief or theory expressed herein.

In an improvement to the above-mentioned process for preparing the catalyst, the first stage, i.e. the reaction stage, in the process is conducted in the presence of an effective amount of a crystal habit modifier, specifically a cationic phase transfer agent or nonionic surfactant. By so doing, the reaction product precipitates in a form that is much easier and quicker to separate from the reaction mixture. In the original process, filtration would be extremely slow, but as a result of addition of the cationic or nonionic additives, the product is at least partially crystalline. The amount of additive to employ is to some extent at the discretion of the user. A convenient amount can be selected in the region of from about 3 to 30% by weight, based on the weight of hydrated zirconium oxychloride employed.

The additive is conveniently an onium compound and especially an ammonium or phosphonium compound. It is particularly desirable to select a tetraalkyl ammonium compound or a derivative of an alkyl substituted N-containing heterocyclic aromatic or alicyclic compound, the compound often containing from about 10 to about 30 carbons in total. Some desirable phase transfer agents comprise alkyl pyridinium salts, such as C12 to C18 pyridinium salts. The counterion is selected such as to impart solubility in the aqueous reaction medium, for example phosphate, sulphate or halide, e.g. chloride or bromide. The nonionic surfactant is conveniently an ethoxylated fatty alcohol, ethoxylated fatty acid, ethoxylated alkylphenol or condensation product of ethylene and/or propylene glycol, for example as described by A. Davidsohn and B. M. Milwidsky in "Synthetic Detergents", 6th edition (1978), George Godwin Limited/John Wiley & Sons.

The selection of catalyst form tends to affect the distribution of products obtained by hydroxylation of the substrate. The use of amorphous zirconium phosphate as catalyst tends to generate substantially similar proportions of ortho and para substituted products, such as hydroquinone and catechol from phenol. On the other hand, a microcrystalline zirconium phosphate tends to favour the production of the ortho substituent, such as for example from about 3:2 to 2:1 catechol:hydroquinone from phenol.

The amount of catalyst to employ is, at least to some extent, at the discretion of the operator. In conjunction with the solvent system described hereinafter, the catalyst is substantially insoluble. Accordingly, it can be readily separated from the reaction mixture and re-used. It is often convenient to employ from 1 to 20 parts w/w of catalyst per 100 parts of substrate.

The solvent system employed in the present invention process contains essentially an aliphatic carboxylic acid. Conveniently, an aqueous solution containing at least 15% v/v carboxylic acid may be employed, and preferably at least 80% v/v. The carboxylic acid preferably contains from 1 to 6 carbon atoms and is, especially suitably, acetic acid.

The amount of hydrogen peroxide to employ is at the discretion of the user. To some extent, the selectivity of the reaction is better when a comparatively low mole ratio of hydrogen peroxide to substrate is employed, but the conversion of the substrate, e.g. phenol, is lower so that a higher proportion remains for processing subsequently. On the other hand if a higher mole ratio of hydrogen peroxide to substrate is employed, the conversion of substrate is higher, but the selectivity tends to be impaired. The mole ratio of hydrogen peroxide: substrate in the reaction mixture is often selected in the range of 0.05:1 to 2:1, and in many instances from about 0.1:1 to about 1:1. Most acceptable results have been obtained in the region of about 0.2:1 to about 0.6:1.

The hydrogen peroxide can be introduced into the reaction mixture in a variety of different ways. In one way, it can all be introduced in a single shot, though for safety's sake it preferably takes from 5 to 15 minutes. In a second way, it can be introduced incrementally, in for example from 2 to 25 increments. In a third way it can be introduced continuously. Its period of introduction may extend to the entire reaction period, if desired. It is most convenient to employ concentrated hydrogen peroxide, of for example from 30 to 75% w/w.

The reaction is suitably conducted at an elevated temperature, that most conveniently is selected in the range of from 45° to 95° C., and especially from 50° to 90° C. It will be recognised that there is a tendency for greater selectivity towards hydroxylation at lower reaction temperatures and a tendency towards a higher reaction rate at higher temperatures within the aformentioned range. The reaction is preferably permitted to continue until all the hydrogen peroxide has been consumed. The overall reaction period will depend upon the interaction of at least three factors, namely the reaction temperature, mole ratio of $H_2O_2$:substrate and nature of the substrate. For an equimolar reaction, the reaction period often lies within the range of 3 to 12 hours, and to a first approximation, a pro rata period can be employed for other mole ratios, though in many embodiments the reaction is permitted to last for a period of from about 4 to about 6 hours, irrespective of the mole ratio employed.

At the end of the reaction period, the solid particulate catalyst can be recovered by conventional separation methods, including filtration and centrifugation. The solvent, substrate and reaction products may be separated by conventional distillation or fractionation techniques. The recovered substrate and solvent can be recycled so as to maximise the overall conversion of substrate to products and minimise solvent costs.

Having described the present invention in general terms, specific embodiments thereof will now be described in greater detail by way of example only.

EXAMPLES 1 TO 5

In these Examples, the catalysts employed were made as follows:

A batch of amorphous zirconium phosphate was made by the first stage of the two stage method of A. Clearfield and D. S. Thakur as referred to hereinbefore. One fraction was retained, dried overnight at about 100° C., and designated AM. The remainder was converted to a microcrystalline form by digesting water-washed solid filtrate under reflux in concentrated phosphoric acid for 72 hours. The water washed product was dried overnight at 100° C. to yield a material designated MC100 and fractions thereof were heated for 2 hours at 200°, 300° or 400° C., designated respectively MC200, MC300 and MC400.

In each of Examples 1 to 5, phenol (9.4 g, 0.1M) was dissolved in acetic acid (50 ml), particulate catalyst (0.5 g) was introduced and the mixture heated to 90° C. Aqueous hydrogen peroxide (35% w/w, 10 g, 0.1M) was introduced with stirring over about an hour and the reaction mixture was maintained at 90° C. for a further 4 hours. The cooled reaction mixture was stored in a tared bottle.

For analysis, a carefully weighed sample of about 0.25 g was diluted to 50 ml and 20 yl was injected into an HPLC, $C_{18}$ column and compared with a standard solution containing hydroquinone, 10 mg, catechol, 10 mg, and phenol, 30 mg, in 50 ml. The solvent mixture/gradient system was:

Solvent A—2% Acetic acid in acetonitrile;
Solvent B—2% aqueous acetic acid;
15% A/85% B on injection of sample altered progressively to 55% A/45% B over 10 minutes.

The eluent was analysed at 280 nm using a diode array detector.

The results for the various catalysts are summarised in Table 1 below. The term % selectivity herein indicates the molar proportion of the specified product on the basis of all products and by-products. Para herein indicates hydroquinone, ortho indicates catechol and total indicates the combined proportions of the two desired products, viz hydroquinone and catechol.

TABLE 1

| Ex. No. | Catalyst | % phenol converted | % Selectivity para | % Selectivity ortho | % Selectivity total |
| --- | --- | --- | --- | --- | --- |
| 1 | AM | 34 | 29 | 27 | 56 |
| 2 | MC100 | 47.5 | 18.5 | 29.5 | 48 |
| 3 | MC200 | 42.5 | 23.5 | 37.5 | 61 |
| 4 | MC300 | 44 | 21 | 37 | 58 |
| 5 | MC400 | 42 | 18.5 | 28.5 | 47 |

From the Table, it can be seen that the most active catalyst was MC100 which converted the highest proportion of phenol. None the less, all the catalysts converted at least one third of phenol. In addition, the selectivity of production of desired products was around 50% or better. It can further be seen that the amorphous catalyst yielded approximately the same proportion of hydroquinone and catechol whereas the microcrystalline catalyst yielded a greater proportion of catechol, in the region of about 63%.

EXAMPLES 6 TO 8

In these Examples, the procedure of Example 2 was followed, i.e. using catalyst MC100, but at the differing reaction conditions and with the results specified in Table 2 below.

TABLE 2

| Ex No | Cat Amnt g | Reaction Time hrs | Reaction Temp °C. | Mole Ratio $H_2O_2$:Phenol | % phenol convertd | % Selectivity para | % Selectivity ortho | % Selectivity total |
|---|---|---|---|---|---|---|---|---|
| 6 | 0.5 | 5 | 90 | 0.5:1 | 34 | 23.5 | 36.5 | 60 |
| 7 | 0.5 | 6 | 50 | 0.5:1 | 13.3 | 36 | 54 | 90 |
| 8 | 0.25 | 4 | 90 | 0.2:1 | 9.9 | 33 | 54.5 | 87.5 |

From Table 2, it can be seen that the selectivity of conversion of phenol to the desired products was improved by employing a lower mole ratio of hydrogen peroxide to phenol and by operating at the lower reaction temperature of 50° C.

EXAMPLES 9 AND COMPARISONS C10 AND C11

In Example 9 and Comparison C10, Example 2 was repeated, but replacing acetic acid by respectively a 20% w/w solution of acetic acid in water or solely water as the solvent. In Comparison C11, Example 2 was repeated, but omitting the catalyst. Any other changes are summarised in Table 3 below.

TABLE 3

| Ex No | Cat Amnt g | Reactn Time hrs | Mole Ratio $H_2O_2$:Phenol | % phenol convertd | % Selectivity para | % Selectivity ortho | % Selectivity total |
|---|---|---|---|---|---|---|---|
| 9 | 0.5 | 6 | 0.5:1 | 11.6 | 33 | 40 | 73 |
| C10 | 0.5 | 5 | 0.5:1 | 0 | 0 | 0 | 0 |
| C11 | — | 5 | 0.5:1 | 19 | 8 | 8 | 16 |

From Table 3, it can be seen that the presence of as small a proportion as 20% acetic acid in the solvent enabled the desired hydroxylation reaction to occur, whereas if water alone was employed as the solvent, no discernible reaction occurred. When the catalyst was omitted, some reaction did occur, but the selectivity to the hydroxylated products was unacceptably low at only 16%.

EXAMPLES 12 TO 14

In these Examples, an improved method of production of the catalyst was carried out. Water, 100 ml, phosphoric acid, 90% $H_3PO_4$, 100 ml and a cationic or nonionic crystal habit modifier, 6 g, were stirred vigorously in a beaker. The crystal habit modifiers were respectively cetyl pyridinium chloride in Example 12, tricaprylylmethyl ammonium chloride available under the tradename ALIQUAT 336 in Example 13 and an ethoxylated alcohol, a nonionic surfactant available under the tradename ETHYLAN CD919 in Example 14. Thereafter, Zirconium oxychloride, $ZrOCl_2.8H_2O$, 40 g, was introduced slowly and the mixture stirred for a further 1 hour. The resultant product was filtered under reduced pressure, taking about 10 minutes and washed with water twice to remove any residual agent. The washed solid, which contained microcrystalline material, was oven dried overnight at about 100° C.

EXAMPLES 15 TO 17

In these Examples, the process of Example 2 was followed, but employing respectively the catalysts produced in Examples 12, 13 and 14 in Examples 15, 16 and 17 and using a reaction period of 6 hours instead of hours. The results are summarised in Table 4 below.

TABLE 4

| Ex. No. | Catalyst product of | % phenol converted | % Selectivity para | % Selectivity ortho | % Selectivity total |
|---|---|---|---|---|---|
| 15 | Ex 12 | 37.5 | 22 | 41.5 | 63.5 |
| 16 | Ex 13 | 39 | 19.5 | 33.5 | 53 |
| 17 | Ex 14 | 42.5 | 19 | 30 | 49.5 |

From Table 4, it can be seen that the catalysts were similarly effective to those produced by the previously known and slower method.

EXAMPLE 18

In this Example, the process of Example 6 was repeated, but employing an alternative substrate, anisole instead of phenol. The results are summarised in Table 5 below.

TABLE 5

| Ex. No. | Substrate | % substrate converted | % Selectivity 4-OH | % Selectivity 2-OH | % Selectivity total |
|---|---|---|---|---|---|
| 18 | Anisole | 19.5 | 16 | 42 | 58 |

From Table 5, it can be seen that the process was effective for the substrate tested.

EXAMPLES 19 AND 20

In Example 19, the catalyst employed was a further sample of microcrystalline zirconium phosphate obtained by the process of Example 12.

In Example 20, the catalyst comprised the catalyst which had already been used in Example 19, filtered from the reaction mixture, washed with methanol and then air dried at 100° C.

In each Example of Examples 19 and 20, phenol was hydroxylated employing the process of Example 2, except for terminating the reaction after 4 rather than 5 hours. The results are tabulated below.

TABLE 6

| Ex. No. | % phenol converted | % Selectivity | | |
|---|---|---|---|---|
| | | para | ortho | total |
| 19 | 32 | 21 | 32 | 53 |
| 20 | 35 | 20 | 28 | 48 |

From Table 6, it can be seen that the catalyst had retained very good productivity and selectivity during its re-use.

We claim:

1. In a process for the hydroxylation of a phenol or phenolic ether wherein a phenol or phenolic ether substrate is reacted with hydrogen peroxide in a solvent in the presence of a catalyst to produce a monohydroxylated phenol or phenolic ether, the improvement wherein the solvent comprises an aliphatic carboxylic acid and wherein the catalyst comprises amorphous or microcrystalline zirconium phosphate.

2. A process according to claim 1 wherein said substrate contains a benzene nucleus.

3. A process according to claim 1 wherein the substrate is mono-nuclear.

4. A process according to claim 2 wherein the substrate benzene nucleus is substituted by a single hydroxyl or ether.

5. A process according to claim 4 wherein the substrate is a phenol.

6. A process according to any of claims 1, 3, 2, 4, or 5 wherein the catalyst comprises microcrystalline zirconium phosphate.

7. A process according to claim 6 wherein the catalyst is obtained by digesting amorphous zirconium phosphate in concentrated phosphoric acid.

8. A process according to claim 6 wherein the catalyst is obtained by reacting zirconium oxychloride ($ZrOCl_2$) with phosphoric acid in the presence of an effective amount of a cationic phase transfer agent or a nonionic surfactant, thereby precipitating zirconium phosphate at least partially in a microcrystalline form.

9. A process according to claim 7 wherein the microcrystalline zirconium phosphate is at least partially dehydrated before use.

10. A process according to claim 9 wherein the catalyst is dehydrated at a temperature of up to about 300° C.

11. A process according to claim 10 wherein the dehydration temperature is selected in the range of from 50° to about 300° C.

12. A process according to claim 1, 3, 2, 4 or 5 wherein the catalyst is employed in an amount of from 1 to 20 parts w/w per 100 parts of the substrate.

13. A process according to claim 1, 3, 2, 4 or 5 wherein the carboxylic acid contains from 1 to 6 carbon atoms.

14. A process according to claim 13 wherein the carboxylic acid comprises acetic acid.

15. A process according to claim 1, 3, 2, 4 or 5 wherein said solvent comprises an aqueous solution containing at least 20% w/w of an aliphatic carboxylic acid.

16. A process according to claim 13 wherein the concentration of carboxylic acid is at least 15% v/v.

17. A process according to claim 1, 3, 2, 4 or 5 wherein the hydroxylation reaction is conducted at a temperature of from 45° to 95° C.

18. A process according to claim 1, 3, 2, 4 or 5 wherein the hydroxylation reaction employs hydrogen peroxide in a mole ratio to substrate in a range of from 0.,05:1 to 2:1.

19. A process according to claim 18 wherein said mole ratio is from 0.1:1 to about 1:1.

20. A process for preparing a catalyst suitable for hydroxylating a phenol or related aromatic compound in which zirconium oxychloride ($ZrOCl_2$) is reacted with excess phosphoric acid in an aqueous medium, thereby precipitating zirconium phosphate wherein the reaction is conducted in the presence of an effective amount of a crystal habit modifier selected from a cationic phase transfer agent or a nonionic surfactant, whereby at least a fraction of the zirconium phosphate precipitates in microcrystalline form.

21. A process for preparing a catalyst according to claim 20 wherein the cationic transfer agent is a tetraalkyl quaternary ammonium salt or an alkylpyridinium salt and the nonionic surfactant is an alcohol ethoxylate.

22. Microcrystalline zirconium phosphate produced by a process according to claim 20.

23. Microcrystalline zirconium phosphate produced by a process according to claim 21.

* * * * *